US006395287B1

(12) United States Patent
Miyauchi et al.

(10) Patent No.: US 6,395,287 B1
(45) Date of Patent: May 28, 2002

(54) LOTIONS CONTAINING VITAMIN D3 DERIVATIVES

(75) Inventors: Eiichi Miyauchi; Yasuyuki Sakai; Keiko Sano, all of Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/988,367

(22) Filed: Nov. 19, 2001

Related U.S. Application Data

(63) Continuation of application No. 09/555,815, filed as application No. PCT/JP98/05535 on Dec. 8, 1998.

(30) Foreign Application Priority Data

Dec. 9, 1997 (JP) .............................................. 9-338813
Dec. 9, 1997 (JP) .............................................. 9-338814

(51) Int. Cl.[7] .......................... A61K 7/48; A61K 31/59
(52) U.S. Cl. ....................................... 424/401; 514/167
(58) Field of Search ........................... 424/401; 514/167

(56) References Cited

U.S. PATENT DOCUMENTS

| 4,866,048 A | 9/1989 | Calverly et al. |
| 4,871,723 A | 10/1989 | Makino et al. |
| 5,362,719 A | 11/1994 | Godtfredsen |
| 5,645,852 A | 7/1997 | Newmark |

FOREIGN PATENT DOCUMENTS

| JP | 5 504959 | 7/1993 |

*Primary Examiner*—Jose G. Dees
*Assistant Examiner*—Mina Haghighation
(74) *Attorney, Agent, or Firm*—Browdy and Neimark, P.L.L.C.

(57) ABSTRACT

The present invention aims to provide a lotion stably maintaining maxacalcitol and having excellent percutaneous absorption. The present invention provides lotions comprising maxacalcitol as an active ingredient and a nonionic surfactant as an additive, as well as lotions which further contains a polyhydric alcohol and a solubilizer as additives besides a nonionic surfactant.

3 Claims, No Drawings

LOTIONS CONTAINING VITAMIN D3 DERIVATIVES

The present application is a continuation of parent copending application Ser. No. 09/555,815, the national stage under 35 USC 371 of International application PCT/JP98/05535 filed Dec. 8, 1998, which designated the United States and was not published in the English language.

FIELD OF THE INVENTION

The present invention relates to lotions stably containing maxacalcitol, which are useful as external medicines. More specifically, the present invention relates to lotions useful as external medicines wherein chemical stability and percutaneous absorption of maxacalcitol as an active ingredient can be controlled by regulating the composition of components.

BACKGROUND ART

Some classes of active vitamin $D_3$ derivatives such as 1α,3β-dihydroxy-20α-(3-hydroxy-3-methylbutyloxy)-9,10-seco-5,7,10(19)-pregnatriene (22-oxa-1α, 25-dihydroxyvitamin $D_3$; herein also referred to as maxacalcitol) have skin epidermal cell growth-inhibiting and differentiation-inducing effects and are expected to have pharmacological effects against psoriasis (JPA Nos. 267550/86 and 183534/88).

Maxacalcitol is known to be chemically unstable and rapidly decompose especially in aqueous solutions. Generally, the following techniques have been proposed to improve stabilization of vitamin D-related derivatives.

(1) stabilization by adding various amino acids (alanine, valine, lysine, etc.: JPA No. 17/87);
(2) stabilization by combination of ascorbic acid or a salt thereof with a chelating agent (JPA No. 44845/86);
(3) stabilization by adding ascorbic acid alone (JPA No. 238936/93); and
(4) stabilization by inclusion in cyclodextrin (JPA Nos. 83021/88 and 128417/76).

However, these techniques have disadvantages such as they involve a complex procedure or have an insufficient stabilization effect, and do not suffice to prepare a lotion stably maintaining maxacalcitol.

As to percutaneous absorption in the category of biological properties, the use of absorption promoters is recommended and the addition of unsaturated fatty acids such as oleic acid or the use of chemicals such as AZONEs has been reported (Morimoto et al. in the program and abstracts of lectures, p. 21, Proceedings of the eighth transdermal therapeutic system symposium, Tokyo, Feb. 21, 1996).

However, these absorption enhancers are not preferable for use in preparations that are often administered (applied) repeatedly, because their enhancing mechanisms depend on providing high absorption efficiency by damaging the skin.

Thus, the need to develop lotions stably maintaining maxacalcitol and having excellent percutaneous absorption continue to exist.

DISCLOSURE OF THE INVENTION

As for the behavior of its stability in aqueous solutions, maxacalcitol is known to remain stable if the pH of the solutions is shifted to an alkaline side. However, alkaline preparations are highly irritant to skin and side effects possibly increase. Therefore, when maxacalcitol is formulated in preparations for external medication, it is desirable to attain stabilization of maxacalcitol in a solution at or around neutral pH.

An object of the present invention is to provide a lotion wherein maxacalcitol as an active ingredient is stably maintained, especially a lotion having a pH at or around neutrality.

Another object of the present invention is to simply solve the problem of chemical stabilization of maxacalcitol, which could not be readily attained in the prior art, by a convenient method of adding a specific type of nonionic surfactant and a polyhydric alcohol.

Still another object of the present invention is to provide a lotion having particularly excellent percutaneous absorption by regulating the compounded amount of a less skin-irritating polyhydric alcohol to control the percutaneous absorption.

As a result of careful studies conducted to solve the above problems, we unexpectedly found that a lotion containing maxacalcitol as an active ingredient stably maintains the active ingredient even at or around neutral pH upon addition of a specific nonionic surfactant. The present invention successfully achieved not only solubilization of oil-soluble materials but also a high stabilization effect by using a specific type of nonionic surfactants among which have heretofore been used as solubilizers for materials that are slightly soluble in water. This was a quite unexpected discovery because no report had been made of the ability of any nonionic surfactants to simultaneously achieve both solubilization and stabilization of oil-soluble materials (maxacalcitol in the specification). Moreover, we succeeded in controlling both of heat stability and percutaneous absorption of the active ingredient maxacalcitol by selecting a polyhydric alcohol, a nonionic surfactant and a solubilizer as additives in a lotion, and also succeeded in establishing an optimal composition for both heat stability and percutaneous absorption in a lotion prepared from specific components. The present invention was completed based on these findings.

Accordingly, the present invention provides a lotion comprising maxacalcitol as an active ingredient and a nonionic surfactant as an additive.

According to a preferred embodiment of the present invention, an ether-type surfactant is used as a nonionic surfactant.

According to a more preferred embodiment of the present invention, a block copolymer-type nonionic surfactant or a polyoxyethylene alkyl ether is used as an ether-type surfactant.

According to a still more preferred embodiment of the present invention, a Pluronic-type or polyoxyethylene cetyl ether-type surfactant is used as an ether-type surfactant.

Preferably, Pluronic™ F-68 or Cetomacrogol™ 1000 is used as a Pluronic-type or polyoxyethylene cetyl ether-type surfactant, respectively.

More preferably, a lotion of the present invention contains 0.1–20% by weight of Pluronic F-68 or 0.1–2% by weight of Cetomacrogol 1000 as a surfactant.

Most preferably, a lotion of the present invention contains 1–5% by weight of Pluronic F-68 or 0.5–2% by weight of Cetomacrogol 1000 as a surfactant.

According to one embodiment of the present invention, there is provided a lotion which, besides a nonionic surfactant, further comprises a polyhydric alcohol and a solubilizer as additives.

Preferably, a lotion of the present invention contains a glycol as a polyhydric alcohol, an ether-type surfactant as a nonionic surfactant and a monohydric alcohol as a solubilizer.

More preferably, a lotion of the present invention contains propylene glycol and/or 1,3-butylene glycol as a polyhydric alcohol, a polyoxyethylene alkyl ether or a Pluronic-type surfactant as a nonionic surfactant and ethanol or isopropanol as a solubilizer.

More preferably, a lotion of the present invention contains propylene glycol and 1,3-butylene glycol as polyhydric alcohols, Cetomacrogol 1000 as a nonionic surfactant and ethanol as a solubilizer.

An especially preferred lotion of the present invention contains 1–70% by weight of propylene glycol, 1–45% by weight of 1,3-butylene glycol, 0.1–5% by weight of Cetomacrogol 1000, 1–20% by weight of ethanol, and the balance being water.

An especially preferred lotion of the present invention contains 50–70% by weight of propylene glycol, 1–20% by weight of 1,3-butylene glycol, 0.1–2% by weight of Cetomacrogol 1000, 1–20% by weight of ethanol, and the balance being water.

Most preferably, a lotion of the present invention contains 50–70% by weight of propylene glycol, 1–20% by weight of 1,3-butylene glycol, 1% by weight of Cetomacrogol 1000, 1% by weight of ethanol, and the balance is water.

PREFERRED EMBODIMENTS OF THE INVENTION

The present invention relates to lotions comprising maxacalcitol as an active ingredient and a nonionic surfactant as an additive, as well as lotions which, besides a nonionic surfactant, further contain a polyhydric alcohol and a solubilizer as additives.

$1\alpha,3\beta$-Dihydroxy-$20\alpha$-(3-hydroxy-3-methylbutyloxy)-9,10-seco-5,7,10(19)-pregnatriene (22-oxa-$1\alpha$,25-dihydroxyvitamin $D_3$; herein also referred to as maxacalcitol) contained as an active ingredient in lotions of the present invention is a known vitamin $D_3$ derivative and can be synthesized by the process described in JPA No. 267550/86, for example.

The amount of maxacalcitol contained in lotions of the present invention is a therapeutically effective amount for the skin disease to be treated, normally within the range of from about 1 $\mu$g/g to about 200 $\mu$g/g, preferably about 2 $\mu$g/g to about 100 1 $\mu$g/g.

Nonionic surfactants used in the present invention have generally been used as solubilizers for slightly soluble materials. According to the present invention, however, nonionic surfactants are added not only to solubilize oil-soluble materials but also to improve heat stability of the active ingredient maxacalcitol. Therefore, the type of nonionic surfactants is not specifically limited in so far as they can simultaneously achieve solubilization and stabilization of the active ingredient maxacalcitol, but ether-type surfactants are preferred.

Among ether-type surfactants, Pluronic-type surfactants (polyoxyethylene/polyoxypropylene glycol) classified into block copolymer-type nonionic surfactants or polyoxyethylene alkyl ethers are especially preferred.

Specific examples of Pluronic-type surfactants include F-68 (trade name of polyoxyethylene (160)/polyoxypropylene (30) glycol available from Asahi Denka Kogyo K.K.) having hydrophilic physical properties. F-68 brings about advantageous effects typically at 0.1–20% by weight, preferably at 1–5% by weight.

Specific examples of polyoxyethylene alkyl ethers include Cetomacrogol 1000 belonging to cetyl ethers. Cetomacrogol 1000 brings about advantageous effects typically at 0.1–2% by weight, preferably at 0.5–2% by weight.

As described above, nonionic surfactants function to both stabilize and solubilize the active ingredient maxacalcitol in lotions of the present invention.

Moreover, by adding the above nonionic surfactants in lotion the pH of preparations can be adjusted to at or around neutrality without decreasing thermal stability of maxacalcitol. The above nonionic surfactants act to physically stabilize external medicines in general, and emulsion-type medicines in particular, so that they are well suitable for incorporation into lotions from both aspects of widely usage as pharmaceutical excipient and material cost.

However, the other class of nonionic surfactants, i.e. ester-type surfactants (polyoxyethylene fatty acid esters) showed contrastive results in maxacalcitol stabilization effect as compared to their satisfactorily solubilization effect. Thus, surfactants can be differentiated by differences of properties in terms of chemical structures.

According to one embodiment of the present invention, the lotion further comprises a polyhydric alcohol and a solubilizer as additives besides a nonionic surfactant.

Polyhydric alcohols suitable for lotions of the present invention have such physical properties that they are generally added as wetting (moisturizing) agents in conventional external preparations. In the present invention, they are added not only for this function but also to control or improve thermal stability of the active ingredient maxacalcitol.

The type of polyhydric alcohols is not specifically limited so far as they can control or improve thermal stability of the active ingredient maxacalcitol, but dihydric alcohols are preferred. Examples of dihydric alcohols include glycols such as propylene glycol, 1,3-butylene glycol, etc.

Solubilizers suitable for lotions of the present invention are reagents for solubilizing the active ingredient maxacalcitol. Solubilizers include, for example, monohydric alcohols such as ethanol or isopropanol. A preferred solubilizer is ethanol.

The ranges of the proportions of specific components in which both thermal stability and percutaneous absorption can be controlled in lotions of the present invention are as follows.

As to Cetomacrogol 1000 among polyoxyethylene cetyl ethers, both of-the above properties can be controlled at a proportion of 0.1–5% by weight.

As to ethanol, both of the above properties can be controlled at a proportion of 1–20% by weight.

As to propylene glycol, both of the above properties can be controlled at a proportion of 0–70% by weight.

As to 1,3-butylene glycol, both of the above properties can be controlled at a proportion of 0–45% by weight.

Pharmaceutical properties and specific proportions of various additives are described below as a guide to a proposal of optimal pharmaceutical formulations.

As to Cetomacrogol 1000, 0.1–2% by weight is a suitable proportion considering both stability and percutaneous absorption.

As to ethanol, 1–20% by weight is a suitable proportion considering both stability and percutaneous absorption.

Propylene glycol mainly has effect on percutaneous absorption and may be added at a variable proportion up to 70% by weight based on actual application in external medicines. Proportions of 0–50% by weight are suitable for preparations that are required to have low absorption, while proportions of 50–70% by weight are suitable for preparations that are required to have high absorption. However, it should be noted that propylene glycol has a concentration-dependent negative effect on thermal stability of maxacalcitol in contrast with its percutaneous absorption.

1,3-Butylene glycol mainly has effect on thermal stability and may be added at any concentration up to 45% by weight based on actual application in external medicines. However, it should be noted that considering percutaneous absorption, 1,3-butylene glycol has no effect when high percutaneous absorption is required.

As described above, propylene glycol and 1,3-butylene glycol have conflicting pharmaceutical properties, so they can be added either alone or in combination in any proportions based on their contributory properties described above in accordance with the method and purpose of use.

For example, preparations having both high chemical stability and high percutaneous absorption as recommended herein contain, as base material, 50–70% by weight of propylene glycol, 0–20% by weight of 1,3-butylene glycol, 0.1–2% by weight, preferably 1% by weight, of Cetomacrogol 1000, and 1–20% by weight, preferably 1% by weight, of ethanol.

The above formulations are generally applicable in the field of external medicines from both aspects of application in products and product economy and their practical feasibility is very high.

If necessary, lotions of the present invention may further contain preservatives such as paraoxybenzoic acid esters and sorbic acids, or additives for improving commercial quality including thickeners such as CMC-Na, wetting (moisturizing) agents, organoleptic agents such as menthol, isopropanol, etc.

The process for preparing lotions of the present invention is not specifically limited. For example, a specific amount of maxacalcitol is dissolved in a specific amount of a solubilizer such as ethanol. In a separate step, a specific amount of a nonionic surfactant is dissolved in an appropriate buffer (such as phosphate buffer). Then, the above two solutions are mixed into a lotion. Alternatively, a mixture of the above two solutions may optionally be combined with a specific amount of a polyhydric alcohol and finally made up with the same buffer to give a lotion.

Lotions of the present invention can be used to treat various cases of psoriasis such as *psoriasis vulgaris, psoriasis pustulosa, psoriasis guttata, erythroderma psoriaticum, psoriasis arthropathica, psoriasis gravis*. The dose depends on the condition of the disease or other factors, but preferably a lotion containing 1 µg/g to 200 µg/g of maxacalcitol is administered once to several times per day.

The following examples further illustrate the present invention without limiting the same thereto.

EXAMPLES

Example A-1

Lotions Containing a Nonionic Surfactant as an Additive

General Preparation Process

A process for preparing a lotion of the present invention is described below. At first, a specified amount of maxacalcitol stock is dissolved in a specified amount of ethanol in accordance with Test formulations in the following Table A-1 (solution 1). In a separate step, a specified amount of each surfactant is dissolved in 25 mM phosphate buffer (pH 8) (solution 2). Then, solution 1 is mixed into solution 2 to prepare a test sample.

Test Formulations

Test formulations are shown in the following Table A-1.

TABLE A-1

| Test example | Maxacalcitol | EtOH | F-68* | Cetomacrogol 1000 | TL-10** | TO-10M*** | PBS (to make) |
|---|---|---|---|---|---|---|---|
| A-1 | 10 µg | 10 µl | 0 g | 0 g | 0 g | 0 g | 1 g |
| A-2 | 10 µg | 10 µl | 1 mg | 0 g | 0 g | 0 g | 1 g |
| A-3 | 10 µg | 10 µl | 5 mg | 0 g | 0 g | 0 g | 1 g |
| A-4 | 10 µg | 10 µl | 10 mg | 0 g | 0 g | 0 g | 1 g |
| A-5 | 10 µg | 10 µl | 0 g | 1 mg | 0 g | 0 g | 1 g |
| A-6 | 10 µg | 10 µl | 0 g | 5 mg | 0 g | 0 g | 1 g |
| A-7 | 10 µg | 10 µl | 0 g | 10 mg | 0 g | 0 g | 1 g |
| A-8 | 10 µg | 10 µl | 0 g | 0 g | 1 mg | 0 g | 1 g |
| A-9 | 10 µg | 10 µl | 0 g | 0 g | 5 mg | 0 g | 1 g |
| A-10 | 10 µg | 10 µl | 0 g | 0 g | 10 mg | 0 g | 1 g |
| A-11 | 10 µg | 10 µl | 0 g | 0 g | 0 g | 1 mg | 1 g |
| A-12 | 10 µg | 10 µl | 0 g | 0 g | 0 g | 5 mg | 1 g |
| A-13 | 10 µg | 10 µl | 0 g | 0 g | 0 g | 10 mg | 1 g |

*F-68: Trade name of polyoxyethylene (160)/polyoxypropylene (30) glycol available from Asahi Denka Kogyo K.K.
**TL-10: Trade name of polysorbate 20 available from Nikko Chemicals Co., Ltd.
***TO-10M: Trade name of polysorbate 80 available from Nikko Chemicals Co., Ltd.

Test Examples

In order to verify and examine the effect of nonionic surfactants, test examples having the above formulations were evaluated for the residual maxacalcitol ratios in percentages vs. initial amount over time (1, 2 and 4 weeks) at a constant temperature of 60° C. in a ventilated incubator. The results are shown in Table A-2.

TABLE A-2

| Test example | Residual ratio (percentage vs. initial amount) | | |
|---|---|---|---|
| | 1 week | 2 weeks | 3 weeks |
| A-1 | 94.22 | 92.29 | 83.52 |
| A-2 | 91.64 | 92.34 | 86.74 |
| A-3 | 92.29 | 92.25 | 89.13 |
| A-4 | 92.98 | 93.16 | 92.63 |
| A-5 | 98.64 | 95.67 | 91.78 |
| A-6 | 98.01 | 99.05 | 94.25 |
| A-7 | 98.28 | 99.44 | 95.88 |

TABLE A-2-continued

| Test example | Residual ratio (percentage vs. initial amount) | | |
|---|---|---|---|
| | 1 week | 2 weeks | 3 weeks |
| A-8 | 89.86 | 89.84 | 84.43 |
| A-9 | 83.46 | 72.20 | 56.64 |
| A-10 | 63.52 | 6.52 | 3.20 |
| A-11 | 91.11 | 74.34 | 44.23 |
| A-12 | 72.07 | 3.95 | 0.00 |
| A-13 | 49.01 | 3.32 | 0.00 |

The above test examples show that addition of nonionic surfactants, especially ether-type surfactants (Test examples A2–A7) has dramatic effect for improving stability as compared with ester-type surfactants (Test examples A8–A13) and a control containing no surfactant (Test example A-1).

Example B-1

Example B-1 relates to various classes of polyhydric alcohols.

(1) Preparation Process

A process for preparing a lotion of the present invention is described below. At first, a specific amount of maxacalcitol is dissolved in a specific amount of ethanol (solution 1). In a separate step, a specific amount of a surfactant (Cetomacrogol 1000) is dissolved in 25 mM phosphate buffer (pH 8) (solution 2). Then, solution 1 is mixed into solution 2 (solution 3). Solution 3 is combined with a specific amount of a polyhydric alcohol and made up with the same buffer to give a test sample.

Test formulations as prepared are shown in the following Table B-1.

TABLE B-1

| Test example | Maxacalcitol | EtOH | Cetomacrogol 1000 | PG | 1,3-butylene glycol | Glycerin | Buffer (to make) |
|---|---|---|---|---|---|---|---|
| B-1 | 50 μg | 10 μl | 10 mg | 450 mg | — | — | 1 g |
| B-2 | 50 μg | 10 μl | 10 mg | — | 450 mg | — | 1 g |
| B-3 | 50 μg | 10 μl | 10 mg | — | — | 450 mg | 1 g |

EtOH: Ethanol
PG: Propylene Glycol (2) Thermal Stability Test

Then, a thermal stability test was performed as follows. In this test, test samples as prepared above were evaluated for the residual maxacalcitol ratios in percentage vs. initial amount over time at each temperature setting in a ventilated incubator.

The obtained thermal stability data are shown in the following Table B-2.

TABLE B-2

| Storage conditions | Evaluation of thermal stability: residual ratio vs. initial amount (%) | | |
|---|---|---|---|
| | Test example | | |
| | B-1 | B-2 | B-3 |
| 1 week, 80° C. | 61.8 | 76.7 | 14.3 |
| 2 weeks, 60° C. | 89.1 | 99.5 | 84.0 |
| 4 weeks, 60° C. | 75.0 | 89.4 | 62.7 |

The data in Table B-2 show that the order of contribution to stabilization in terms of thermal stability is 1,3-butylene glycol>propylene glycol>glycerin. Especially effective was 1,3-butylene glycol.

(3) Percutaneous Absorption Test

A percutaneous absorption test was performed as follows. As test animals, 6-week old male SD rats were conditioned at a constant temperature and a constant humidity (25° C., 50–60% RH) for a week and subjected to experiments at the age of 7 weeks.

The administration method is as follows. On the day before administration, rats are cervicodorsally shaved with a clipper and a shaver and conditioned in separate cages for a day. On the day of administration, a single dose of 15 μg/0.3 g lotion /kg of each test sample is percutaneously administered at an area of 3×4 cm on the shaved part. At hours 4 and 24 after administration, the lotion is wiped off with absorbent cotton soaked in 70% ethanol and a skin section is cut out from the wiped site as a test sample.

The absorbent cotton was assayed for the amount of unabsorbed maxacalcitol. Unabsorbed ratios were expressed as the percentages of the amounts recovered vs. administered amount and evaluated.

The results are shown in Table B-3. Evaluation was made for unabsorbed maxacalcitol ratios (%) at hours 4 and 24. Each value represents mean±SE.

TABLE B-3

| Period after administration | Evaluation of percutaneous absorption: unabsorbed maxacalcitol ratio (%) | | |
|---|---|---|---|
| | Test example | | |
| | B-1 | B-2 | B-3 |
| 4 hours | 69.77 ± 4.76 | 81.74 ± 1.89 | 80.38 ± 3.16 |
| 24 hours | 41.56 ± 3.98 | not evaluated | 50.53 ± 2.38 |

As is apparent from Table B-3, percutaneous absorption as demonstrated by the order of contribution to initial uptake (up to 4 hours) among various base materials showed that glycerin and 1,3-butylene glycol have comparable effects while propylene glycol has more positive effects than the other two base materials.

Example B-2

Example B-2 examines the amount of propylene glycol, which was shown to have good percutaneous absorption in Example B-1.

The process for preparation of test formulations, thermal stability test method, percutaneous absorption test method and the like were as described in Example B-1.

Test formulations of Example B-2 are shown in the following Table B-4.

TABLE B-4

| Test example | Maxacalcitol | Ethanol | Cetomacrogol 1000 | Propylene glycol | PBS (to make) |
|---|---|---|---|---|---|
| B-4 | 50 μg | 10 μl | 10 mg | 200 mg | 1 g |
| B-5 | 50 μg | 10 μl | 10 mg | 450 mg | 1 g |
| B-6 | 50 μg | 10 μl | 10 mg | 700 mg | 1 g |

The data for thermal stability of the formulations of Example B-2 are shown in the following Table B-5.

TABLE B-5

Evaluation of thermal stability: residual ratio vs. initial amount (%)

| Storage conditions | Test example | | |
|---|---|---|---|
| | B-4 | B-5 | B-6 |
| 2 weeks, 60° C. | 94.0 | 89.1 | 85.4 |
| 4 weeks, 60° C. | 90.1 | 75.0 | 69.3 |

As for the contribution to stabilization in terms of thermal stability, propylene glycol showed a concentration-dependent negative effect on chemical stability of maxacalcitol.

The results of percutaneous absorption test are shown in Table B-6. Evaluation was made for unabsorbed maxacalcitol ratios (%) 4 hours after administration. Each value represents mean±SE.

TABLE B-6

Evaluation of percutaneous absorption:

| | Test example | | |
|---|---|---|---|
| | B-4 | B-5 | B-6 |
| Unabsorbed maxacalcitol ratio (%) | 71.44 ± 1.479 | 69.77 ± 4.764 | 62.21 ± 3.800 |

As to percutaneous absorption, the order of contribution to initial uptake (up to 4 hours) among base materials was in contrast with the results of thermal stability test and this shows the tendency that the amount of addition of propylene glycol has a positive effect on percutaneous absorption.

Example B-3

Example B-3 is intended to make a closer investigation of a 70% propylene glycol formulation.

The formulation was as shown in Test example B-6 of Example B-2, and the preparation process, thermal stability test and percutaneous absorption test were as described in Example B-1. During percutaneous absorption test, the amount of unabsorbed maxacalcitol was determined from the absorbent cotton used for wiping off maxacalcitol and the amount of maxacalcitol in the skin was determined from the skin section cut out. Unabsorbed ratios and skin residual ratios were expressed as the percentages of the respective amounts recovered vs. administered amount and evaluated by comparison.

Formulations of Example B-3 are shown in the following Table 7.

TABLE B-7

| Test example | Maxacalcitol | Ethanol | Cetomacrogol 1000 | Propylene glycol | PBS (to make) |
|---|---|---|---|---|---|
| B-7 | 50 μg | 10 μl | 10 mg | 700 mg | 1 g |

The data for thermal stability of the formulation of Example B-3 are shown in the following Table B-8.

TABLE B-8

Evaluation of thermal stability: residual ratio (% vs. initial amount)

| Period (weeks) | Storage temperature and residual ratio (% vs. initial amount) | | | |
|---|---|---|---|---|
| | 80° C. | 60° C. | 40° C. | 25° C. |
| 2 | 45.3 | 85.4 | 99.2 | — |
| 4 | — | 69.3 | 98.3 | — |
| 12 | — | 69.3 | 96.0 | — |
| 24 | — | 53.6 | 91.4 | 101.0 |

Long-term prediction from the above data by Arrhenius calculation indicated that the expected period for 95% storage at 25° C. was 2.7 years whereas the expected residual ratio at 25° C. for 2 years was 98.1%. Thus, the results of Arrhenius prediction on thermal stability suggest that the tested formulation can be stored at room temperature.

The data from the percutaneous absorption test on the formulation of Example B-3 are shown in Table B-9. Evaluation was made for unabsorbed maxacalcitol ratios and maxacalcitol ratios in skin after 4 and 24 hours.

TABLE B-9

Evaluation of percutaneous absorption: (Example B-3: on formulation of Test example B-7) (indicated in mean ± SE)

| Time (hour) | Unabsorbed maxacalcitol ratio | Maxacalcitol ratio in skin |
|---|---|---|
| 0 | 100% | 0% |
| 4 | 49.70% ± 2.855 | 14.31% ± 1.077 |
| 24 | 34.68% ± 2.175 | 16.62% ± 1.032 |

As to percutaneous absorption, the initial uptake process was very rapid and subcutaneous retentivity was good. The formulation of Test example B-7 proved to well satisfy the requirements for rapid delivery and retention at the target site, which are essential to the contemplated type of external medicines.

These results demonstrate that the formulation of Test example B-7 satisfies physicochemical or biological requirements of external medicines and therefore has a satisfactory commercial value.

Example B-4

Example B-4 relates to mixed systems of polyhydric alcohols (propylene glycol and 1,3-butylene glycol). The results of the above Examples B1 to B3 showed that 1,3-butylene glycol and propylene glycol are effective for thermal stability and percutaneous absorption, respectively. In Example B-4, the two components were combined so as to control both pharmaceutical properties simultaneously with a view to constructing more ideal formulations.

Composite experimental design was used to estimate formulations for simultaneously optimizing both pharmaceutical properties of thermal stability and percutaneous absorption. Specifically, mathematical functions each obtained from a certain matrix experiment conducted to determine the relationship between the blend ratio of base materials and the values of the pharmaceutical properties of the resulting formulation are coordinated and the resulting single coordinated function is solved to search for the required formulation. Such a technique for formulation design may be useful in the respect of study efficiency or the like. However, it should be noted that this composite experimental design is generally applicable and herein constitutes only a means for leading to the present invention but does not have any novelty.

The preparation process, thermal stability test and percutaneous absorption test were conducted as described in Example B-1.

Formulations prepared in Example B-4 are shown in the following Table B-10.

The following Table B-11 shows the results of the thermal stability test and percutaneous absorption test on the formulations of Example B-4. The thermal stability test was based on the evaluation of residual ratios (%) vs. initial amount at 40° C. for 12 weeks and percutaneous absorption test was based on the evaluation of unabsorbed maxacalcitol ratios (%) vs. the initial amount 4 hours after administration.

TABLE B-11

| Test example | Thermal stability test 40° C., 12 weeks (%) | Percutaneous absorption test Unabsorbed maxacalcitol ratio after 4 hours (%) |
|---|---|---|
| B-8 | 97.8 | 76.5 |
| B-9 | 96.6 | 72.5 |
| B-10 | 96.6 | 67.6 |
| B-11 | 94.3 | 68.1 |
| B-12 | 97.8 | 79.9 |
| B-13 | 97.5 | 88.8 |
| B-14 | 96.5 | 74.6 |
| B-15 | 94.4 | 62.7 |
| B-16 | 97.2 | 80.6 |
| B-17 | 97.1 | 77.5 |
| B-18 | 95.2 | 76.2 |
| B-19 | 94.4 | 70.4 |
| B-20 | 97.4 | 80.6 |
| B-21 | 96.4 | 73.9 |
| B-22 | 97.0 | 74.1 |
| B-23 | 95.0 | 69.9 |
| B-24 | 96.3 | 66.0 |
| B-25 | 96.2 | 68.5 |
| B-26 | 97.9 | 88.2 |
| B-27 | 92.7 | 68.0 |
| B-28 | 95.8 | 67.1 |
| B-29 | 96.1 | 79.7 |

TABLE B-10

| Test example | Maxacalcitol (µg) | Cetomacrogol 1000 (mg) | EtOH (µl) | PG (mg) | 1,3-butylene glycol (mg) | PBS to make (g) |
|---|---|---|---|---|---|---|
| B-8 | 50 | 20 | 60 | 229 | 171 | 1 |
| B-9 | 50 | 20 | 60 | 343 | 57 | 1 |
| B-10 | 50 | 20 | 60 | 343 | 257 | 1 |
| B-11 | 50 | 20 | 60 | 514 | 86 | 1 |
| B-12 | 50 | 40 | 60 | 229 | 171 | 1 |
| B-13 | 50 | 40 | 60 | 343 | 57 | 1 |
| B-14 | 50 | 40 | 60 | 343 | 257 | 1 |
| B-15 | 50 | 40 | 60 | 514 | 86 | 1 |
| B-16 | 50 | 20 | 160 | 229 | 171 | 1 |
| B-17 | 50 | 20 | 160 | 343 | 57 | 1 |
| B-18 | 50 | 20 | 160 | 343 | 257 | 1 |
| B-19 | 50 | 20 | 160 | 514 | 86 | 1 |
| B-20 | 50 | 40 | 160 | 229 | 171 | 1 |
| B-21 | 50 | 40 | 160 | 343 | 57 | 1 |
| B-22 | 50 | 40 | 160 | 343 | 257 | 1 |
| B-23 | 50 | 40 | 160 | 514 | 86 | 1 |
| B-24 | 50 | 30 | 110 | 214 | 286 | 1 |
| B-25 | 50 | 30 | 110 | 500 | 0 | 1 |
| B-26 | 50 | 30 | 110 | 214 | 86 | 1 |
| B-27 | 50 | 30 | 110 | 500 | 200 | 1 |
| B-28 | 50 | 10 | 110 | 357 | 143 | 1 |
| B-29 | 50 | 50 | 110 | 357 | 143 | 1 |
| B-30 | 50 | 30 | 10 | 357 | 143 | 1 |
| B-31 | 50 | 30 | 210 | 357 | 143 | 1 |
| B-32 | 50 | 30 | 110 | 357 | 143 | 1 |
| B-33 | 50 | 30 | 110 | 357 | 143 | 1 |
| B-34 | 50 | 30 | 110 | 357 | 143 | 1 |

EtOH: Ethanol
PG: Propylene Glycol

TABLE B-11-continued

| Test example | Thermal stability test 40° C., 12 weeks (%) | Percutaneous absorption test Unabsorbed maxacalcitol ratio after 4 hours (%) |
|---|---|---|
| B-30 | 95.9 | 66.5 |
| B-31 | 94.3 | 79.6 |
| B-32 | 95.4 | 66.4 |
| B-33 | 96.7 | 86.1 |
| B-34 | 95.8 | 73.4 |

The results of Example B-4 suggested that both thermal stability and percutaneous absorption can be improved even if the amounts of Cetomacrogol 1000 and ethanol are held at the necessary minimums.

Example B-5

Formulations for Simultaneous Optimization

Formulations shown in the following Table B-12 were prepared to ultimately optimize the amounts of propylene glycol and 1,3-butylene glycol based on the results of Example B-4.

TABLE B-12

| Test example | Maxacalcitol (μg) | Cetomacrogol 1000 (mg) | EtOH (μl) | PG (mg) | 1,3-butylene glycol (mg) | PBS to make (g) |
|---|---|---|---|---|---|---|
| B-35 | 50 | 10 | 10 | 171 | 229 | 1 |
| B-36 | 50 | 10 | 10 | 214 | 286 | 1 |
| B-37 | 50 | 10 | 10 | 257 | 343 | 1 |
| B-38 | 50 | 10 | 10 | 300 | 400 | 1 |
| B-39 | 50 | 10 | 10 | 400 | 300 | 1 |
| B-40 | 50 | 10 | 10 | 500 | 200 | 1 |
| B-41 | 50 | 10 | 10 | 600 | 100 | 1 |

EtOH: Ethanol
PG: Propylene Glycol

The following Table B-13 shows the results of a percutaneous absorption test. Evaluation was made for the unabsorbed amount of maxacalcitol vs. the administered amount of maxacalcitol at hours 4 in percentage thereof.

TABLE B-13

| | Test example | | | | | | |
|---|---|---|---|---|---|---|---|
| | B-35 | B-36 | B-37 | B-38 | B-39 | B-40 | B-41 |
| Unabsorbed rate (%) | 78.5 | 70.4 | 65.2 | 70.6 | 66.0 | 52.2 | 51.7 |

Since optimal formulations to be proposed should have good absorption, the above Formulations B-40 and B-41 were further examined as follows.

A thermal stability test was conducted on the above Test examples B-40 and B-41 over time and the results are shown in the following Table B-14.

TABLE B-14

| Test example | Thermal stability test: residual rate vs. initial amount (%) | | |
|---|---|---|---|
| | 60° C., 2 weeks | 60° C., 1 month | 40° C., 1 month |
| B-40 | 99.0 | 99.7 | 99.7 |
| B-41 | 99.0 | 99.9 | 100.1 |

The data for percutaneous absorption of the above Test examples B-40 and B-41 over time are shown in Table B-15, which represents unabsorbed ratios and residual ratios in skin of maxacalcitol at hour 2, 4 and 24 (together with the data for the above 70% propylene glycol formulation as a control for comparison). Each value represents mean±SE.

TABLE B-15A

| | Unabsorbed maxacalcitol remaining in lotions (%) | | |
|---|---|---|---|
| | Test example | | |
| Time (hour) | B-40 | B-41 | Control |
| 0 | 100 | 100 | 100 |
| 2 | 56.6 ± 2.8 | 66.4 ± 6.7 | 78.3 |
| 4 | 58.8 ± 3.8 | 54.6 ± 3.6 | 49.8 ± 2.8 |
| 24 | 40.4 ± 1.3 | 39.2 ± 4.1 | 34.7 ± 2.2 |

TABLE B-15B

| | Maxacalcitol absorbed into skin (%) | | |
|---|---|---|---|
| | Test example | | |
| Time (hour) | B-40 | B-41 | Control |
| 0 | 0 | 0 | 0 |
| 2 | 14.0 ± 2.5 | 8.0 ± 0.6 | 19.0 |
| 4 | 13.0 ± 2.6 | 18.0 ± 0.2 | 14.3 ± 1.1 |
| 24 | 23.5 ± 3.1 | 20.3 ± 1.2 | 16.6 ± 1.0 |

Dramatic improvements in thermal stability were observed in the heat acceleration test as compared with the 70% propylene glycol formulation; percutaneous absorption was also significant as demonstrated by very rapid initial uptake comparable to that of the 70% propylene glycol formulation and by good retention in the target skin site. Thus, the formulations of Test examples B-40 and B-41 were proved to well satisfy the requirements for rapid delivery and retention at the target site, which are essential to the contemplated type of external medicines.

INDUSTRIAL APPLICABILITIES

According to the present invention, thermal stability and percutaneous absorption can be efficiently controlled by regulating the amounts of common base materials; furthermore, formulations based on the control can also be proposed. This control of pharmaceutical properties proved to lead to efficient proposal of desired optimal formulations in accordance with the purpose and method of use.

Recently, some classes of activated vitamin $D_3$ derivatives, particularly maxacalcitol, are expected to bring about topical pharmacological effects against psoriasis based on their skin epidermal cell growth-inhibiting and differentiation-inducing effects; they are also expected to achieve systemic pharmacological effects such as PTH secretion/production-inhibiting effects and differentiation-inducing effects and immunoregulation effects. This suggests that absorption control in external application is very important for attaining pharmaceutical efficacy of medicines having both systemic and topical pharmacological effects. The present invention also proposes a solution to this technical issue.

As a result of mainly controlling percutaneous absorption by changing the amounts of components, optimal formulations required in the respects of pharmaceutical efficacy or side-effects can be proposed; therefore formulations for different purposes such as external medicines for topical or systemic application can potentially be proposed.

Thus, the present invention provides lotions useful as external medicines wherein chemical stability and percutaneous absorption of maxacalcitol as an active ingredient can be controlled by regulating the composition of components.

What is claimed is:

1. A lotion comprising
   (1) maxacalcitol as an active ingredient; and
   (2) polyoxyethylene cetyl ether in an amount of 0.5–2% by weight.
2. A lotion comprising
   (1) maxacalcitol as an active ingredient; and
   (2) polyoxyethylene/polyoxypropylene glycol in an amount of 0.1–20% by weight.
3. The lotion of claim 2, wherein said polyoxyethylene/polyoxypropylene glycol is polyoxyethylene(160)/polyoxypropylene(30) glycol.

* * * * *